United States Patent [19] [11] 4,138,482
Dostert [45] Feb. 6, 1979

[54] 3-CYANO-N-(N,N-DIMETHYLAMINO-PROPYL)-IMINODIBENZYL AND SALTS THEREOF

[75] Inventor: Philippe Dostert, Chaville, France

[73] Assignee: Hoffmann-La Roche Inc., Nutley, N.J.

[21] Appl. No.: 840,790

[22] Filed: Oct. 11, 1977

[30] Foreign Application Priority Data

Oct. 12, 1976 [CH] Switzerland .................... 12876/76

[51] Int. Cl.[2] .................... A61K 31/55; C07D 223/28
[52] U.S. Cl. ............................ 424/244; 260/239 D
[58] Field of Search .................. 260/239 D; 424/244

[56] References Cited

FOREIGN PATENT DOCUMENTS

| | | | |
|---|---|---|---|
| 1359676 | 4/1964 | France. | |
| 84219 | 12/1964 | France. | |
| 375360 | 4/1964 | Switzerland | 260/239 |

OTHER PUBLICATIONS

Jacob et al., Compt. Rend. vol. 252, #14, p. 2117 (1961).

*Primary Examiner*—Donald G. Daus
*Assistant Examiner*—D. B. Springer
*Attorney, Agent, or Firm*—Jon S. Saxe; George M. Gould; William G. Isgro

[57] ABSTRACT

3-Cyano-N-(N,N-dimethylaminopropyl)-iminodibenzyl, and its salts, prepared, inter alia, by heating 3-cyano-iminodibenzyl-5-carboxylic acid (N,N-dimethylaminopropyl ester) are described. The end product and its salts are useful as antidepressants.

3 Claims, No Drawings

3-CYANO-N-(N,N-DIMETHYLAMINOPROPYL)-IMINODIBENZYL AND SALTS THEREOF

BRIEF SUMMARY OF THE INVENTION

The iminodibenzyl derivatives of the present invention comprises the compound 3-cyano-N-(N,N-dimethylaminopropyl)-iminodibenzyl of the formula

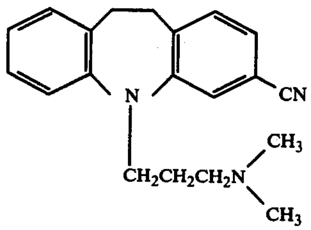

I and its pharmaceutically acceptable acid addition salts.

DETAILED DESCRIPTION OF THE INVENTION

The invention relates to 3-cyano-N-(N,N-dimethylaminopropyl)-iminodibenzyl of the formula

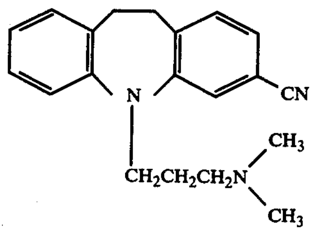

I and its pharmaceutically acceptable acid addition salts.

The 3-cyano-N-(N,N-dimethylaminopropyl)-iminodibenzyl of formula I and its pharmaceutically acceptable acid addition salts, are distinguished by a strong antidepressive activity which primarily manifests itself in animal experiments in an extraordinarily strong inhibition of the neuronal serotonin uptake. The compound of formula I and its pharmaceutically acceptable acid addition salts, are therefore useful, for example, for the treatment of depressions of endogenous or exogenous origin. More specifically, they are useful as antidepressants. Advantageously, anticholinergic side-effects, which can manifest themselves, for example, in mouth dryness, constipation, tachycardia and/or accommodation disorders, are confined to a minimum in the compound of formula I and its salts.

In accordance with the present invention, 3-cyano-N-(N,N-dimethylaminopropyl)-iminodibenzyl and its pharmaceutically acceptable acid addition salts are prepared by (a) reacting a compound of the formula

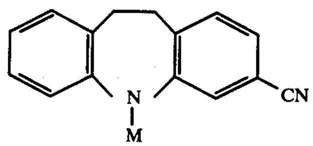

II wherein M is an alkali metal atom, with a compound of the formula

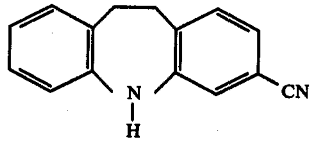

III wherein Z is a leaving atom or group, or (b) reacting 3-cyano-iminodibenzyl of the formula

IV

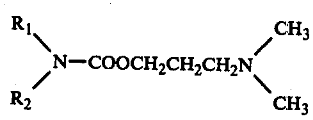

with a compound of the formula

V wherein $R_1$ and $R_2$, independently, are hydrogen or lower alkyl, or $R_1$ and $R_2$, taken together with the nitrogen atom to which they are attached, are a 5-membered or 6-membered saturated heterocyclic group, or (c) heating 3-cyano-iminodibenzyl-5-carboxylic acid (N,N-dimethylaminopropyl ester) of the formula

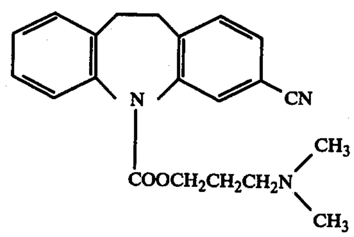

VI or (d) reacting 3-bromo-N-(N,N-dimethylaminopropyl)-iminodibenzyl of the formula

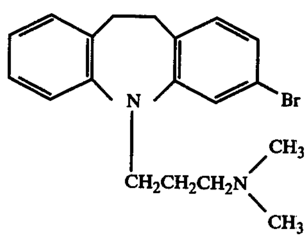

VII with copper-I-cyanide, and if desired, converting the base of formula I obtained into a pharmaceutically acceptable acid addition salt.

The 3-cyano substituted starting materials of formulas II and IV can be prepared from iminodibenzyl. The latter is converted into 5-acetyl-iminodibenzyl by heating with acetyl chloride in an inert organic solvent, such as toluene. The 5-acetyl-iminodibenzyl is transformed into 5-acetyl-3-oxalyl-iminodibenzyl by means of a Friedel-Crafts reaction. For this purpose, the 5-acetyl-iminodibenzyl is reacted with an oxalic mono(-lower alkyl) ester chloride, preferably oxalic acid monomethyl ester chloride, in the presence of a Friedel- Crafts catalyst, for example, aluminum trichloride, in an inert solvent, preferably methylene chloride or carbon disulfide, preferably at room temperature. The 3-oxalyl group of the resulting 5-acetyl-3-oxalyl-iminodibenzyl is partly esterified. To completely hydrolyze this ester to the α-keto acid, the reaction product is subjected to an acidic or alkaline hydrolysis. It is preferred to subject the reaction product to an alkaline hydrolysis; for example, at room temperature in the presence of aqueous sodium hydroxide and methanol. The acetyl group in the resulting 5-acetyl-3-oxalyl-iminodibenzyl is removed by hydrolysis; for example, by treatment with an alkali metal hydroxide in water or in a monohydroxy or polyhydroxy alcohol at a temperature which should preferably be elevated, for example, the boiling point of the mixture. The resulting 3-oxalyl-iminodibenzyl is converted by treatment with a hydroxylamine acid addition salt, for example, hydroxylamine hydrochloride, and acetic acid into the corresponding 3-oxime acid derivative. This treatment is preferably carried out under weak alkaline, buffered conditions. For the work-up, the mixture is acidified, following which the 3-oxime acid derivative can be extracted from the aqueous phase with an inert organic solvent, such as, tetrahydrofuran. The organic phase is subsequently introduced dropwise into water and the 3-oxime acid derivative is converted into 3-cyano-iminodibenzyl. The temperature at which this is carried out is preferably at about 90° to about 100° C.

Since 3-cyano-iminodibenzyl is only weakly basic, it is preferably converted into an alkali metal derivative of formula II prior to the reaction with a starting material of formula III. This conversion is preferably carried out by treatment with, for example, an alkali metal amide or alkali metal hydride, such as sodium, potassium or lithium hydride or amide. The treatment is preferably carried out in an aprotic solvent, preferably in a polar aprotic solvent, such as dimethylformamide. The treatment is preferably carried out at a temperature in the range of from about 20° to about 100° C., most preferably at about 50° C.

The leaving atom or group denoted by Z in the starting materials of formula III is preferably a halogen atom or lower alkyl- or lower aryl-substituted sulfonyloxy group. The lower alkyl or lower aryl groups present in the substituted sulfonyloxy groups, preferably contain from 1 to 4 or 6 to 10 carbon atoms, respectively, and are, in particular, methyl or phenyl or p-tolyl. The term "halogen" preferably denotes chlorine or bromine, especially chlorine.

The reaction of a compound of formula II with a compound of formula III can be carried out in an inert aprotic solvent, preferably in an inert polar aprotic solvent such as, dimethylformamide. The reaction is preferably carried out at a temperature in the range of from about 20° C. to about 100° C., most preferably at about 50° C.

In the starting materials of formula V, lower alkyl groups denoted by $R_1$ or $R_2$ are preferably alkyl groups containing from 1 to 4 carbon atoms, for example, methyl, ethyl, isopropyl or n-butyl. When $R_1$ and $R_2$ together with the nitrogen atom to which they are attached are a 5-membered or 6-membered, saturated heterocyclic group, such a group can be, for example, piperidino, pyrrolidino, morpholino, or the like.

The reaction of 3-cyano-iminodibenzyl of formula IV with a compound of formula V is preferably carried out in the absence of a solvent at a temperature in the range of from about 200° C. to about 280° C., most preferably at about 250° C. The reaction can be carried out under reduced pressure, if desired. It is preferred to carry out the reaction in the presence of a basic catalyst, for example, an alkali metal salt of a weak acid, such as the sodium or potassium salt of acetic acid, formic acid, carbonic acid, phthalic acid, or the like.

The 3-cyano-iminodibenzyl-5-carboxylic acid (N,N-dimethylaminopropyl ester) starting material of formula VI also forms part of the present invention. It can be prepared by the action of phosgene on 3-cyano-iminodibenzyl and the subsequent reaction of the resulting 3-cyano-5-chlorocarbonyl-iminodibenzyl with dimethylaminopropanol.

The heating of 3-cyano-iminodibenzyl-5-carboxylic acid (N,N-dimethylaminopropyl ester) of formula VI is preferably carried out at a temperature in the range of from about 150° C. to about 250° C., most preferably under reduced pressure. The desired 3-cyano-N-(N,N-dimethylaminopropyl)-iminodibenzyl of formula I is obtained directly in this manner.

The 3-bromo-N-(N,N-dimethylaminopropyl)-iminodibenzyl starting material of formula VII can be prepared from an alkali metal salt of 3-bromo-iminodibenzyl and a compound of formula III in a manner analogous to that described earlier in connection with the reaction of a compound of formula II with a compound of formula III.

The reaction of 3-bromo-N-(N,N-dimethylamino-propyl)-iminodibenzyl of formula VII with copper-I-cyanide is preferably carried out in an aprotic polar organic solvent, such as, dimethylformamide at elevated temperature, preferably at a temperature in the range of about 100° C. to about the boiling point of the reaction mixture. The desired 3-cyano-N-(N,N-dimethylaminopropyl)-iminodibenzyl of formula I is obtained, together with starting material and small amounts of 3-cyano-iminodibenzyl and 3-bromo-iminodibenzyl. The desired 3-cyano-N-(N,N-dimethylaminopropyl)-iminodibenzyl can be separated from the byproducts of the mixture, for example, by extraction in an organic solvent with an aqueous acid and, after alkalization of the aqueous phase, extraction with an organic solvent, removal of the solvent and distillation of the residue.

The 3-cyano-N-(N,N-dimethylaminopropyl)-iminodibenzyl of formula I forms salts with pharmaceutically accetpable inorganic acids, for example, with hydrohalic acids, such as, hydrochloric acid or hydrobromic acid, and with other mineral acids, such as sulfuric acid, phosphoric acid, nitric acid, or the like, and with pharmaceutically acceptable organic acids, for example, tartaric acid, citric acid, camphorsulfonic acid, methanesulfonic acid, toluenesulfonic acid, salicylic acid, ascorbic acid, maleic acid, fumaric acid, mandelic acid, or the like. The preferred salts are the hydrohalides, most preferably the hydrochloride. The acid addition salts are preferably prepared in a suitable solvent such as ethanol, acetone or acetonitrile, by treatment of the free base with the corresponding non-aqueous acid.

The 3-cyano-N-(N,N-dimethylaminopropyl)-iminodibenzyl of formula I is a crystalline solid which has a relatively good solubility in dimethylsulfoxide, dimethylformamide, chlorinated hydrocarbons, such as, chloroform and methylene chloride, alkanols, such as methanol and ethanol, ether and benzene. It is soluble in water with relative difficulty.

The acid addition salts of 3-cyano-N-(N,N-dimethylaminopropyl)-iminodibenzyl of formula I are crystalline solids. They have good solubility in dimethylsulfoxide, dimethylformamide, alkanols, such as methanol and ethanol, chloroform, methylene chloride and water. They are soluble in benzene, ether and n-hexane with relative difficulty.

As mentioned earlier, the iminodibenzyl derivative and its salts provided by the present invention are distinguished by strong antidepressive activity which can be observed, for example, on the basis of the inhibition of the serotonin uptake in the neurones of the brain of the rat. In order to demonstrate this antidepressive activity, 3-cyano-N-(N,N-dimethylaminopropyl)-iminodibenzyl (substance A) was tested against known analogs in accordance with the following experimental procedures:

Substance A

3-Cyano-N-(N,N-dimethylaminopropyl)-iminodibenzyl hydrochloride (a compound of the invention).

Substance B

N-(N,N-Dimethylaminopropyl)-iminodibenzyl hydrochloride (a known compound).

Substance C

3-Chloro-N-(N,N-dimethylaminopropyl)-iminodibenzyl hydrochloride (a known compound).

1. Inhibition of the serotonin uptake in vitro

The uptake of serotonin in the synaptosomes of the forebrain of rats was tested according to J. Pharmacol. exp. Ther. 181, 36, 1972. An inhibition of 50% ($ED_{50}$) could be measured at the following concentrations:

| Substance | $ED_{50}$, mol/liter |
|---|---|
| A | $1.5 \times 10^{-9}$ |
| B | $7.8 \times 10^{-8}$ |
| C | $6.4 \times 10^{-9}$ |

In this test, substance A therefore has a 52 and 4.2 times greater activity than the two known substances B and C, respectively.

2. Inhibition of the serotonin uptake ex vivo

An analogous experimental procedure to that given under 1 was utilized. The test substances were, however, injected intraperitoneally; the serotonin uptake was measured after 1 hour. Untreated rats were used as the controls. The following $ED_{50}$ values could be ascertained:

| Substance | $ED_{50}$, mg/kg. |
|---|---|
| A | 0.9 |
| B | 19.0 |
| C | 2.2 |

In this test, substance A is as active as the two known substances B and C in 21 and 2.4 times smaller doses, respectively.

3. Inhibition of the serotonin re-uptake in vivo

The action of the so-called "membrane pump" was tested according to the method described in Biochem. Pharmacol. 20, 707, 1971. The following $ED_{50}$ values could be ascertained:

| Susbtance | $ED_{50}$, mg/kg. |
|---|---|
| A | 0.7 |
| B | 12.8 |
| C | 6.5 |

In this test, substance A is as active as the two known substances B and C in 18 and 9 times smaller doses, respectively.

The following results for the inhibition of serotonin uptake in blood platelets of the rat are given as further verification of the antidepressive activity of the iminodibenzyl derivative and its salts provided by the invention.

4. Inhibition of the serotonin uptake in vitro 0.5 Ml. of blood plasma was treated with different concentrations of test substance in 50 μl of physiological sodium chloride solution. After incubating at 37° C. for 5 minutes, serotonin ($C^{14}$; 0.1 μM) was added and the mixture was incubated at 37° C. for an additional 5 minutes. The serotonin concentration was determined by means of a $C^{14}$ measuring apparatus. A control experiment in which no test substance is used was also carried out. By varying the concentration of test substance, (three different concentrations) the concentration which leads to a 50% inhibition of the serotonin uptake ($ED_{50}$) was determined.

| Substance | $ED_{50}$, mmol |
|---|---|
| A | 56 |
| B | 7000 |
| C | 1200 |

In this test, substance A has a 130 and 20 times greater activity than the two known substances B and C, respectively.

5. Inhibition of the serotonin uptake in vivo

Rats were given twice daily over a period of 4 days an intraperitoneal injection of 5.0 mg. of test substance per kg. and 12 hours after the last administration the rats were killed. Serotonin was determined spectrofluorimetrically as described in J. Pharmacol. exp. Ther. 117, 82 et seq, 1956, and the protein content was determined colorimetrically as described in J. Biol. Chem. 193, 265 et seq, 1951.

| Substance | Number of rats | Serotonin in mmol/mg. of protein | Inhibition in % of the control |
|---|---|---|---|
| Controls | 24 | $11.25 \pm 1.64$ | |
| A | 12 | $4.09 \pm 1.30$ | 61 |
| B | 9 | $9.72 \pm 2.12$ | 14 |
| C | 9 | $10.91 \pm 2.11$ | 3 |

The iminodibenzyl derivative and its salts can be utilized as medicaments, for example, in the form of pharmaceutical preparations which contain them in association with one or more compatible pharmaceutical carrier materials. A carrier material can be an organic or inorganic inert carrier material suitable for enteral, for example, oral, or parenteral administration, and include, for example, water, gelatin, lactose, starch, magnesium stearate, talc, vegetable oils, gum arabic, polyalkyleneglycols, or the like. The pharmaceutical preparations can be made up in solid form, for example, as tablets, dragees, suppositories or capsules, or in liquid form, for example, as solutions, suspensions or emulsions. The pharmaceutical preparations may be sterilized and/or may contain adjuvants, such as preserving, stabilizing, wetting or emulsifying agents, salts for varying the osmotic pressure or buffers. The pharmaceutical preparations can also contain still other therapeutically valuable substances.

Convenient pharmaceutical dosage forms contain about 1-200 mg. of 3-cyano-N-(N,N-dimethylaminopropyl)-iminodibenzyl of formula I or a pharmaceutically active acid addition salt thereof. Convenient oral dosages are in the range of from about 1 mg/kg per day to about 10 mg/kg per day. Convenient parenteral dosages are in the range of from about 0.1 mg/kg per day to about 1 mg/kg per day. It will be appreciated that the aforementioned dosages are exemplary and can be varied depending on the requirements of the warm-blooded animal being treated.

The following Examples further illustrate the invention. All temperatures are in degrees Centigrade, unless otherwise mentioned.

EXAMPLE 1

Preparation of 3-cyano-N-(N,N-dimethylaminopropyl)-iminodibenzyl hydrochloride 230 G. of 50% sodium hydride in mineral oil, which has been washed three times with 1 liter of n-hexane, and 4.5 liters of dimethylformamide, dried over molecular sieves, are charged into a 20 liter four-necked flask provided with a stirrer, condenser, thermometer and dropping funnel and having inert gasification. To this suspension is added dropwise within about 2 hours at room temperature a solution of 919 g. of 3-cyano-iminodibenzyl in 7 liters of dimethylformamide. The mixture is stirred at 50° C. for 0.5 hour, cooled down and treated dropwise at 20°-25° C. within about 1 hour with a solution of 1120 g. of N,N-dimethylaminopropyl chloride in 2.5 liters of dimethylformamide. The mixture is again warmed to 50° C. and stirred at this temperature for 3 hours. It is subsequently stirred at room temperature overnight. After completion of the reaction, the excess sodium hydride is decomposed by the slow dropwise addition of 2.5 liters of water while blowing nitrogen through the mixture. The mixture is subsequently poured on to 12 liters of ice-water and extracted once with 20 liters and once with 10 liters of ethyl acetate. The ethyl acetate solutions are washed once with 6 liters of water, combined and extracted once with 6 liters of 1-N hydrochloric acid and once with 8 liters of water. The acidic-aqueous phases are adjusted to pH 9 with concentrated sodium hydroxide while cooling with ice. The mixture is extracted once with 20 liters and once with 10 liters of ethyl acetate. The organic phase is washed once with 6 liters of water. The ethyl acetate solution is evaporated in vacuo without drying. The thus-obtained residue is filtered with toluene through 6 kg. of aluminum oxide (activity grade II; neutral). The thin-layer chromatographically uniform fractions are combined and evaporated, and there are obtained about 1230 g. of base. This base is dissolved in 10 liters of isopropanol and treated with 500 ml. of 30% ethanolic hydrochloric acid until a Congo-acidic reaction is obtained. The solution is warmed to 40°-50° C. for 2 hours, the hydrochloride crystallizes out. The mixture is then slowly cooled down to room temperature and subsequently to 0° C. The crystallizate is removed by filtration, washed with 3 liters of ice-cold isopropanol and twice with 2.5 liters of absolute ether each time. The product is dried over potassium hydroxide in a drying oven for 16 hours in vacuo at 40° C., and there is obtained 3-cyano-N-(N,N-dimethylaminopropyl)-iminodibenzyl hydrochloride which, for further purification, is recrystallized as follows:

1095 G. of 3-cyano-N-(N,N-dimethylaminopropyl)-iminodibenzyl hydrochloride are dissolved hot in 2.6 liters of absolute ethanol and treated while stirring with 2.6 liters of absolute ether, the product crystallizes out. It is left to crystallize for an additional 1 hour at room temperature and for 3 hours at 0° C. while stirring. The crystals are removed by filtration under suction, washed with 1.5 liters of ether/ethanol (1:1) and dried at 40° C. in vacuo over potassium hydroxide for 16 hours, and there is obtained 3-cyano-N-(N,N-dimethylaminopropyl)-iminodibenzyl hydrochloride, having a melting point of 200°-202° C.

The 3-cyano-iminodibenzyl utilized as the starting material can be prepared as follows:

585 G. of iminodibenzyl are dissolved in 2000 ml. of toluene in a 6 liter four-necked flask provided with a stirrer, condenser, thermometer and dropping funnel and warmed to 80° C. (internal temperature). 370 Ml. of acetyl chloride are added dropwise at 80° C. within 0.75 hour. The mixture is stirred at 80° C. overnight (or for 16 hours). The mixture is subsequently cooled to room temperature using an ice-bath and the excess acetyl chloride is destroyed by the dropwise addition of 200 ml. of ethanol and 1000 ml. of water. The mixture is also treated with 500 ml. of ether. The aqueous phase is separated and re-extracted once with 1500 ml. of ether. The organic phases are individually washed three times with 1000 ml. of water. The combined organic phases are treated with 50 g. of carbon, dried over sodium sulfate and evaporated to dryness in vacuo. The resulting crude product is dissolved in 1000 ml. of ether while stirring and the solution is stirred overnight, the product crystallizes out. The crystallizate is removed by filtration and washed with a small amount of ice-cold ether, and there are obtained 539 g. of 5-acetyliminodibenzyl having a melting point of 95°-96° C. The mother liquor is evaporated in vacuo and afterwards treated with 200 ml. of ether. This mixture is poured with slight stirring into about 70 ml. of petroleum ether of low boiling point until turbidity sets in and stirred for 4 hours. After suction filtration and washing of the crystallizate with a small amount of cold ether, there is obtained an additional amount of 5-acetyl-iminodibenzyl having a melting point of 94°-96° C.

1800 G. of aluminum chloride in 3600 ml. of methylene chloride, dried over molecular sieves, are charged under an inert gas into a 20 liter round flask provided with a stirrer, condenser, thermometer, dropping funnel with gas-inlet tube and exhaust apparatus for hydrochloric acid gas. To this mixture is added dropwise within about 0.5 hour at room temperature, a solution of 712 g. of 5-acetyl-iminodibenzyl in 1800 ml. of methylene chloride dried over molecular sieves and the resulting mixture is left to stir for approximately an additional 10 minutes. Thereafter, there is added dropwise within 0.5 hour at room temperature a solution of 830 ml. of oxalic acid monomethyl ester chloride and 1200 ml. of methylene chloride. In so doing, the internal temperature slowly rises to 33° C. The mixture is left to stir at room temperature overnight (or during 16 hours). After completion of the reaction, 3000 ml. of 3-N hydrochloric acid are cautiously added dropwise while cooling well with ice so that the temperature does not exceed 20° C. Since, in so doing, the flask content becomes an unstirrable thick mass, it must be diluted with 5000 ml. of ethyl acetate. The mixture is cautiously treated with 2000 ml. of distilled water while stirring intensively. The flask content is transferred to a 30 liter stirring vessel and, after treatment with an additional 5000 ml. of ethyl acetate, stirred. The aqueous phase is re-extracted once with 4000 ml. of ethyl acetate. The organic phases are washed five times with 4000 ml. of dilute sodium chloride solution each time (2000 ml. of saturated aqueous sodium chloride solution and 2000 ml. of water). Concentration is then carried out in vacuo without drying. The water is removed by azeotropic distillation with 1500 ml. of toluene. After completion of the evaporation, there is obtained a resin which is dissolved in 3800 ml. of methanol on a steam-bath and charged into a 20 liter stirring flask. The methanolic solution, cooled with an ice-bath, is treated, with further cooling, with 4550 ml. of 1-N aqueous sodium hydroxide in such a manner that the temperature does not exceed 15° C. After completion of the saponification, the flask content is poured on to 8000 ml. of ice-water and adjusted Congo-acidic with about 850 ml. of concentrated hydrochloric acid while stirring. The mixture is extracted once with 12 liters and once with 4 liters of ethyl acetate. The organic phases are washed individually six times with 4 liters of water. The combined ethyl acetate phases are concentrated in vacuo without drying to a volume of about 1–2 liters, water still remaining is azeotropically removed by distillation with toluene. The crystal mass obtained after concentration is cooled to room temperature while stirring, stirred at this temperature for 2–3 hours and then removed by filtration under suction. The filter cake is washed portionwise with a total of 1 liter of ice-cold ethyl acetate and dried in vacuo at 40° C., whereby there is obtained thin-layer chromatographically uniform 5-acetyl-3-oxalyl-iminodibenzyl having a melting point of about 205° C.

658 G. of potassium hydroxide are dissolved in 5 liters of water in a 20 liter four-necked flask provided with a stirrer, condenser, thermometer and inert gas inlet tube, the temperature rising to about 45° C. 1000 G. of 5-acetyl-3-oxalyl-iminodibenzyl are introduced into this solution with inert gasification and the mixture is left to stir at an oil-bath temperature of 135° C. for about 24 hours until complete saponification is achieved. The flask content is cooled down to room temperature and treated with 100 ml. of ethyl acetate in order to avoid a foam formation. Thereafter, there is added dropwise at 15°–20° C. within 1.5 hours a solution consisting of 2 liters of water, 540 ml. of glacial acetic acid and 448 g. of hydroxylamine hydrochloride. After completion of the addition, the mixture is stirred for 5–5.5 hours and the flask content is stirred into 12 liters of ethyl acetate. The mixture is acidified to pH 1–2 with concentrated hydrochloric acid. The aqueous phase is separated and re-extracted once with 5 liters of ethyl acetate. The organic phases are washed individually five times with 5 liters of water each time (total 25 liters) and then dried over sodium sulfate and evaporated. The thus-obtained crude product is dissolved in 3 liters of tetrahydrofuran and introduced dropwise within about 1.5–2 hours into 12 liters of boiling water in a 20 liter flask while stirring well and simultaneously distilling the tetrahydrofuran, whereby the internal temperature should lie at about 85° C. to about 95° C. Then, there is added dropwise within 0.25 hour a solution of 28.6 g. of hydroxylamine hydrochloride in 200 ml. of water and the mixture is left to stir at 90°–95° C. for 5 hours. In due course there results a resinous rubber-like precipitate and the aqueous phase is clear. When this condition is reached, the mixture is worked-up as follows:

The supernatant aqueous clear solution is removed by decantation and rejected. The residue is dissolved in 12 liters of methylene chloride and washed twice with 5 liters of water each time. The aqueous phases are back-extracted once with 2 liters of methylene chloride. The combined organic phases are concentrated to a volume of about 5 liters, the nitrile crystallizes out. In order to achieve complete crystallization, the mixture is left to stand in a refrigerator overnight and the crystallizate is then removed by filtration. The mother liquor obtained is removed by filtration through a column containing 4.5 kg of aluminum oxide (activity grade II; neutral) with methylene chloride and the thin-layer chromatographically uniform fractions are combined and evaporated in vacuo. The thus-obtained residue is combined with the aforementioned crystallizate and suspended in about 1 liter of ether/methylene chloride (3:1). The suspension is filtered and the crystallizate again back-washed with a small amount of ether/methylene chloride (3:1). After drying in vacuo at 40° C., there is obtained thin-layer chromatographically uniform 3-cyano-iminodibenzyl having a melting point of 164°–165° C.

EXAMPLE 2

Preparation of 3-cyano-N-(N,N-dimethylaminopropyl)-iminodibenzyl 1.10 G. of 3-cyano-iminodibenzyl and 0.25 g. of potassium acetate are heated to 210° C. At this temperature, there is added dropwise within 15 minutes, 1.74 g. of dimethylaminopropyl dimethylcarbamate. The mixture is subsequently heated to 250° C. for 3 hours, and is then cooled down to room temperature. The mixture is treated with 20 ml. of water and extracted twice with 20 ml. of chloroform each time. The combined chloroform phases are washed with 20 ml. of water and the basic constituents are separated from neutral constituents by extraction with 10 ml. of 5% methanesulfonic acid each time. The aqueous phase is now made alkaline with 28% aqueous sodium hydroxide solution and extracted with chloroform. After drying over magnesium sulfate, concentration is carried out under reduced pressure. The residue is distilled at 200° C./0.05 mmHg. The resulting light yellow distillate crystallizes spontaneously, and there is obtained 3-cyano-N-(N,N-dimethylamino-propyl)-iminodibenzyl having a melting point of 55°–57° C.

EXAMPLE 3

Preparation of 3-cyano-N-(N,N-dimethylaminopropyl)-iminodibenzyl 1.30 G. of 3-bromo-N-(N,N-dimethylaminopropyl)-iminodibenzyl and 0.41 g. of copper-I-cyanide are boiled under reflux for 6 hours in the presence of 5 ml. of dimethylformamide. The mixture is cooled down to room temperature. 20 Ml. of chloroform are added thereto and the resulting mixture is filtered. The chloroform phase is washed with water, dried and evaporated.

A brown oil remains as the residue and has the following composition (in accordance with gas chromatography): 72% of 3-cyano-N-(N,N-dimethylaminopropyl)-iminodibenzyl, 4% of 3-bromo-N-(N,N-dimethylaminopropyl)-iminodibenzyl, 16% of 3-cyano-iminodibenzyl and 1% of 3-bromo-iminodibenzyl. Purification of the crude product can be carried out as follows:

The brown oil is dissolved in 20 ml. of chloroform and extracted three times with 10 ml. of 5% methanesulfonic acid. The acidic portion is washed with 20 ml. of ethyl acetate and made alkaline with concentrated aqueous sodium hydroxide. The resulting emulsion is extracted twice with 20 ml. of chloroform each time. The chloroform phases are combined, washed with 50 ml. of water, dried over magnesium sulfate and evaporated under reduced pressure. The oily residue is distilled under strongly reduced pressure, and there is obtained 3-cyano-N-(N,N-dimethylaminopropyl)-iminodibenzyl in the form of a yellow oil having a boiling point of 240° C./0.12 mmHg which crystallizes overnight; melting point 53°-55° C.

The 3-bromo-N-(N,N-dimethylaminopropyl)-iminodibenzyl used as the starting material can be prepared as follows:

1.50 G. of sodium hydride dispersion (50% in mineral oil) are washed with 10 ml. of n-hexane and suspended in 5 ml. of N,N-dimethylformamide. This suspension is added dropwise at room temperature over a period of 10 minutes to a solution of 2.2 g. of 3-bromo-iminodibenzyl in 5 ml. of dimethylformamide. The resulting solution is stirred at 70° C. for 0.25 hour, cooled down to room temperature and treated dropwise with a solution of 3.67 g. of N,N-dimethylaminopropyl chloride in 4 ml. of dimethylformamide. The mixture is stirred at 60° C. for 16 hours and subsequently treated with 40 ml. of water. The resulting emulsion is extracted twice with 20 ml. of ethyl acetate. The ethyl acetate extracts are combined, washed eight times with 50 ml. of water and extracted three times with 20 ml. of 10% methanesulfonic acid. The acidic portion is washed twice with 20 ml. of ethyl acetate and again made alkaline with concentrated sodium hydroxide solution. The basic product is extracted twice with 30 ml. of chloroform, dried over magnesium sulfate and concentrated under reduced pressure. The brown oily residue is distilled under strongly reduced pressure, and there is obtained 3-bromo-N-(N,N-dimethylaminopropyl)-iminodibenzyl having a boiling point of 230° C./0.08 mmHg.

EXAMPLE 4

Preparation of 3-cyano-N-(N,N-dimethylaminopropyl)-iminodibenzyl 1.90 G. of 3-cyano-iminodibenzyl-5-carboxylic acid (N,N-dimethylaminopropyl ester) are heated under reduced pressure to 170° C. for 3 hours and to 210° C. for 1 hour. The brown oil obtained is taken up in 30 ml. of chloroform and extracted twice with 20 ml. of 1-N methanesulfonic acid. The acidic extracts are washed with 30 ml. of ethyl acetate and subsequently made alkaline with concentrated sodium hydroxide solution. The resulting basic product is extracted twice with 20 ml. of chloroform each time. The organic solution is washed with water, dried over magnesium sulfate and evaporated, whereby there is obtained 3-cyano-N-(N,N-dimethylaminopropyl)-iminodibenzyl, having a melting point of 53°-55° C.

The 3-cyano-iminodibenzyl-5-carboxylic acid (N,N-dimethylaminopropyl ester) utilized as the starting material can be prepared as follows:

2.70 G. of 3-cyano-iminodibenzyl are dissolved in 20 ml. of orthoxylene. A light stream of phosgene, dried with sulfuric acid, is conducted into the solution, which is warmed to 100° C., for 7 hours. Subsequently, the solution is stirred at the same temperature for 3 hours and then the solvent is evaporated, and there is obtained 3-cyano-5-chlorocarbonyl-iminodibenzyl, having a melting point of 129°-130° C.

2.89 G. of 3-cyano-5-chlorocarbonyl-iminodibenzyl are dissolved, together with 1.13 g. of 3-dimethylamino-propanol, in 20 ml. of benzene and the mixture is heated under reflux for 18 hours under argon gasification. The resulting solution is made alkaline with 5 ml. of 2-N aqueous sodium hydroxide and washed four times with 70 ml. of water each time. The benzene phase is extracted twice with 50 ml. of 1-N aqueous methanesulfonic acid each time and the aqueous phases are washed with 20 ml. of ethyl acetate. The aqueous phases are combined, made alkaline with concentrated aqueous sodium hydroxide and extracted twice with 30 ml. of chloroform each time. The chloroform phases are combined, washed with water, dried over magnesium sulfate and concentrated under reduced pressure, whereby there is obtained 3-cyano-iminodibenzyl-5-carboxylic acid (N,N-dimethylaminopropyl ester) in the form of a brown oil.

The following Examples illustrate pharmaceutical preparations containing a compound of the present invention and the preparation thereof..

EXAMPLE A

| Preparation of tablets: | |
|---|---|
| 3-cyano-N-(N,N-dimethylaminopropyl)-iminodibenzyl hydrochloride | 50 g. |
| Lactose | 202 g. |
| Maize starch | 80 g. |
| Hydrolyzed maize starch | 20 g. |
| Calcium stearate | 8 g. |
| | 360 g. |

The 3-cyano-N-(N,N-dimethylaminopropyl)-iminodibenzyl hydrochloride, lactose, maize starch and hydrolyzed maize starch are mixed and granulated with water to a viscous paste. This paste is passed through a sieve and subsequently dried at 45° C. overnight. The dried granulate is passed through a sieve and subsequently mixed with the calcium stearate. The mixture obtained is pressed to tablets weighing 360 mg. and having a diameter of about 10 mm.

EXAMPLE B

| Preparation of Tablets: | |
|---|---|
| 3-cyano-N-(N,N-dimethylaminopropyl)-iminodibenzyl hydrochloride | 25.0 g. |
| Lactose | 114.0 g. |
| Maize starch | 50.0 g. |
| Gelatinized maize starch | 8.0 g. |
| Calcium stearate | 3.0 g. |
| | 200.0 g. |

The 3-cyano-N-(N,N-dimethylaminopropyl)-iminodibenzyl hydrochloride, lactose, maize starch and gelatinized maize starch are intimately mixed with one another. The mixture is passed through a comminuting machine and subsequently moistened with water to a thick paste. The moist mass is passed through a sieve. The moist granulate is dried at 45° C. The dried granulate is mixed thoroughly with the calcium stearate, and is pressed to tablets weighing 200 mg. and having a diameter of about 8 mm.

EXAMPLE C

| Preparation of Capsules: | |
|---|---|
| 3-cyano-N-(N,N-dimethylaminopropyl)-iminodibenzyl hydrochloride | 25.0 g. |
| Lactose | 160.0 g. |
| Maize starch | 30.0 g. |
| Talc | 5.0 g. |
| | 220.0 g. |

The 3-cyano-N-(N,N-dimethylaminopropyl)-iminodibenzyl hydrochloride, lactose and maize starch are intimately mixed with one another and passed through a comminuting machine. The mixture is mixed thoroughly with the talc and filled into hard shell gelatin capsules.

EXAMPLE D

| Preparation of a parenteral dosage form: | |
|---|---|
| Each 1 ml. ampul contains: | |
| 3-cyano-N-(N,N-dimethylaminopropyl)-iminodibenzyl hydrochloride | 10.20 mg. (2% excess) |
| Methanesulfonic acid for injection | 2.22 mg. |
| Glucose for injection | 40.0 mg |
| Water for injection q.s. ad | 1 ml |

In a glass vessel, there are dissolved in 8000 ml of water for injection with stirring at room temperature, successively:

22.2 g of methanesulphonic acid for injection,
102 g of active ingredient and
400 g of glucose.

Subsequently, water for injection is added to a total volume of 10,000 ml. The solution is either aseptically filtered, filled into colourless ampoules, gassed with nitrogen and sealed or filled into colourless ampoules, gassed with nitrogen, sealed and subsequently sterilised in a current of steam or autoclaved at 120° C. for 30 minutes.

The above procedure can also be carried out utilising the corresponding amount of hydrochloric acid instead of methanesulphonic acid.

I claim:

1. 3-Cyano-N-(N,N-dimethylaminopropyl)-iminodibenzyl or a pharmaceutically acceptable acid addition salt thereof.

2. In accordance with claim 1, 3-cyano-N-(N,N-dimethylaminopropyl)-iminodibenzyl hydrochloride.

3. A pharmaceutical composition for the treatment of depression consisting essentially of an effective amount of 3-cyano-N-(N,N-dimethylaminopropyl)iminodibenzyl or a pharmaceutically acceptable acid addition salt thereof for the treatment of depression in warm-blooded mammals and a pharmaceutically acceptable carrier material.

* * * * *